United States Patent
Haveri

(10) Patent No.: US 7,918,799 B2
(45) Date of Patent: Apr. 5, 2011

(54) METHOD AND INTERFACE FOR COOLING ELECTRONICS THAT GENERATE HEAT

(75) Inventor: Heikki Antti Mikael Haveri, Palakoskentie (FI)

(73) Assignee: General Electric Company, Schenectady, NY (US)

( * ) Notice: Subject to any disclaimer, the term of this patent is extended or adjusted under 35 U.S.C. 154(b) by 306 days.

(21) Appl. No.: 12/032,957

(22) Filed: Feb. 18, 2008

(65) Prior Publication Data
US 2009/0209863 A1 Aug. 20, 2009

(51) Int. Cl.
*F28D 15/00* (2006.01)
*A61B 8/00* (2006.01)
*A61B 8/12* (2006.01)

(52) U.S. Cl. .................. 600/459; 165/104.19
(58) Field of Classification Search .................. 600/459; 165/104.19
See application file for complete search history.

(56) References Cited

U.S. PATENT DOCUMENTS

| | | | |
|---|---|---|---|
| 4,019,098 A | 4/1977 | McCready et al. | |
| 4,186,422 A | 1/1980 | Laermer | |
| 4,567,770 A * | 2/1986 | Rumbold et al. | 73/644 |
| 4,590,538 A | 5/1986 | Cray, Jr. | |
| 5,057,968 A | 10/1991 | Morrison | |
| 5,063,475 A | 11/1991 | Balan | |
| 5,545,942 A | 8/1996 | Jaster et al. | |
| 5,560,362 A | 10/1996 | Sliwa, Jr. et al. | |
| 5,573,414 A * | 11/1996 | Taillon et al. | 439/191 |
| 5,625,548 A | 4/1997 | Gold et al. | |
| 5,669,813 A | 9/1997 | Jairazbhoy et al. | |
| 5,721,463 A * | 2/1998 | Snyder | 310/334 |
| 5,726,873 A | 3/1998 | Gold et al. | |
| 5,780,928 A | 7/1998 | Rostoker et al. | |
| 5,918,469 A | 7/1999 | Cardella | |
| 5,953,224 A | 9/1999 | Gold et al. | |
| 5,961,465 A | 10/1999 | Kelly, Jr. et al. | |
| 5,966,286 A | 10/1999 | O'Connor et al. | |
| 6,016,007 A | 1/2000 | Sanger et al. | |
| 6,173,759 B1 | 1/2001 | Galyon et al. | |
| 6,175,501 B1 | 1/2001 | Bortolini et al. | |
| 6,213,194 B1 | 4/2001 | Chrysler et al. | |
| 6,396,692 B1 | 5/2002 | Farshi et al. | |
| 6,438,984 B1 | 8/2002 | Novotny et al. | |
| 6,580,609 B2 | 6/2003 | Pautsch | |
| 6,955,215 B2 | 10/2005 | Al-Garni et al. | |
| 6,958,910 B2 | 10/2005 | Tanaka et al. | |
| 7,052,463 B2 | 5/2006 | Peszynski et al. | |
| 7,215,547 B2 | 5/2007 | Chang et al. | |
| 7,252,139 B2 | 8/2007 | Novotny et al. | |
| 7,314,447 B2 | 1/2008 | Park et al. | |
| 7,365,981 B2 | 4/2008 | Myers et al. | |
| 2002/0127900 A1* | 9/2002 | Goodwin et al. | 439/196 |
| 2006/0100513 A1* | 5/2006 | Hashimoto | 600/437 |
| 2006/0173344 A1* | 8/2006 | Marian et al. | 600/459 |
| 2008/0077017 A1* | 3/2008 | Hyuga | 600/459 |

* cited by examiner

*Primary Examiner* — Hezron Williams
*Assistant Examiner* — Rose M Miller
(74) *Attorney, Agent, or Firm* — Dean Small; The Small Patent Law Group

(57) ABSTRACT

A method and interface for cooling electronics that generate heat are provided. The interface includes a housing having tubing (i) therein to transfer heat from liquid flowing in the tubing and (ii) extending therefrom and configured to engage a pump. The tubing forms a closed circulation path. The interface further includes an electrical connection member configured to provide electrical connection through the housing and to the electronics.

22 Claims, 5 Drawing Sheets

METHOD AND INTERFACE FOR COOLING ELECTRONICS THAT GENERATE HEAT

BACKGROUND OF THE INVENTION

One or more embodiments of this invention relate generally to a method and interface for cooling electronics that generate heat, especially electronics in ultrasound and biomedical systems.

As electronic devices are miniaturized, the amount of heat generated by the more densely populated electronics increases. As the amount of generated heat increases, the components within the device also operate at higher temperatures. These higher temperatures can degrade the performance of the devices. Moreover, the increased heat also emanates from the device. Accordingly, in some applications, for example, in medical ultrasound imaging probes that contact individuals during an exam, the increased heat not only can cause injury, but may exceeded acceptable regulatory levels. Accordingly, these devices have to be cooled.

In the medical imaging area, and particularly, in the ultrasound imaging area, heat is often a serious problem as a result of the intense processing that has to be performed at the scan head of the ultrasound probe. The dissipated heat from the scan head (e.g., from the miniaturized electronics in the scan head) needs to be transferred away from the scan head both to ensure the safety of the individual being scanned and to comply with certain regulatory guidelines to maximum heating conditions, which are especially critical when performing obstetrical scans. Additionally, increased heating of the scan head can affect the useful life of the ultrasound probe.

Current methods to dissipate the heat in devices with miniaturized electronics typically include heat sinks or heat exchangers that are complex, large and heavy. Thus, the reduced sized advantage gained from the miniaturized electronics is offset by the heat dissipation components that are needed. These current heat dissipation methods also add time and cost to manufacturing and maintenance, as well as result in a device that is often more cumbersome to use. For example, in ultrasound imaging systems (e.g., 3D ultrasound imaging systems), FR-4 (Flame Retardant 4) material is often used to manufacture the printed circuit boards within the probes of these systems. The processors and miniaturized components on these printed circuit boards generate heat that must be dissipated.

In order to dissipate the heat, these ultrasound imaging systems typically include several electronic circuit boards, for example, eight electronic circuit boards that are successively glued between metallic plates. The metallic plates are in connection with each other through one divergent plate on one side. The parallel metal plates function as cooling ribs for the electronic circuit boards and conduct to the divergent plate the heat dissipated by the electronics. The divergent plate is also connected to an aluminum body or housing. The assembly also may be surrounded in copper or aluminum tape. The aluminum housing includes machined channels to allow fluid flow therethrough. The channels are pneumatically connected to a connector end of a probe of the ultrasound system through tubing. The connector end of the probe includes a diaphragm pump and another aluminum body or liquid tank that is also in pneumatic connection with the tubing. Cooling liquid is circulated inside the tubing by the pump and through the two aluminum bodies (one at the transducer end of the probe and one at the connector end of the probe). This cooling system attempts to transfer heat away from the hand held transducer end to the connector end in order, for example, to meet mandated maximum temperature levels, as well as to improve the operation of the transducer. However, as a result of the different components needed in this cooling assembly, the overall device size and weight is increased, which affects the portability and potential applications for the ultrasound system. Also, the device is often time consuming to manufacture because the manufacturing steps have to be performed by hand. Additionally, the pump has a tendency to leak, which not only reduces the performance of the probe, but requires constant drying or maintenance.

BRIEF DESCRIPTION OF THE INVENTION

In one embodiment, an interface for cooling electronics is provided that includes a housing having tubing (i) therein to transfer heat from liquid flowing in the tubing and (ii) extending therefrom and configured to engage a pump. The tubing forms a closed circulation path. The interface further includes an electrical connection member configured to provide electrical connection through the housing and to the electronics.

In another embodiment, an ultrasound system is provided that includes an ultrasound scanner having a pump and including a connection port. The ultrasound system further includes a probe having a connector including a cooling system therein. The connector is configured to engage the connection port and wherein engagement of the connector with the connection port provides (i) electrical connection between the ultrasound scanner and the probe and (ii) connection of the cooling system to the pump of the ultrasound scanner.

In yet another embodiment, a method of cooling an ultrasound system is provided. The method includes circulating fluid within a closed tubing path that extends from a connector of an ultrasound probe of the ultrasound system to electronics within the ultrasound probe. The fluid is circulated using a pump located within an ultrasound scanner of the ultrasound system. The method further includes thermally connecting tubing within the connector with a housing of the connector and wherein the connector is thermally connected to the ultrasound scanner when the connector of the ultrasound probe engages the ultrasound scanner.

DETAILED DESCRIPTION OF THE INVENTION

Figure 1:
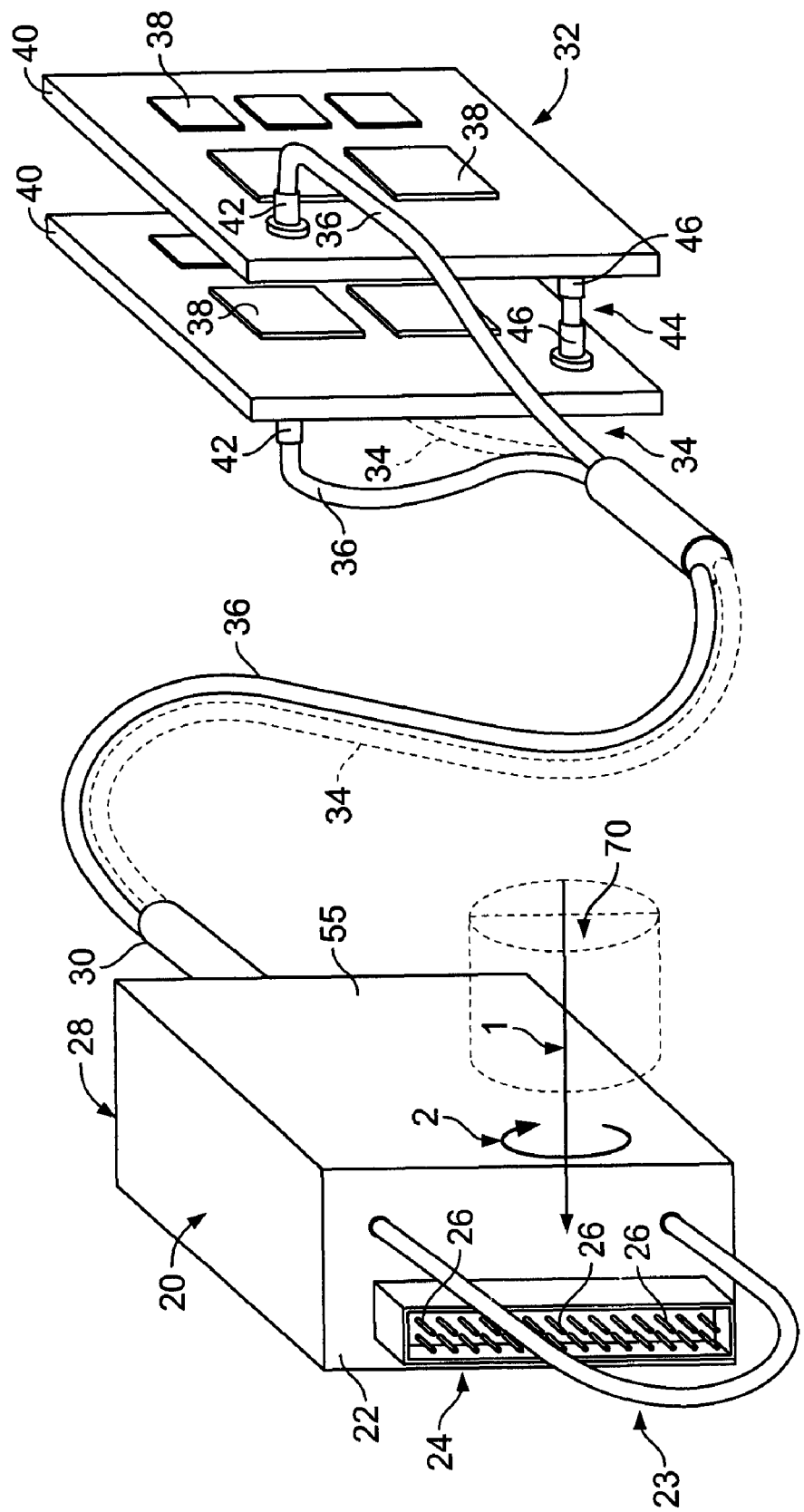
FIG. 1 is a diagram showing an interface constructed in accordance with various embodiments of the invention for cooling electronics.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property. Additionally, the arrangement and configuration of the various components described herein may be modified or changed, for example, replacing certain components with other components or changing the order or relative positions of the components.

Various embodiments of the invention provide an interface, such as a connector that allows cooling of electronics within systems, for example, electronics of printed circuit boards within an ultrasound imaging system. The heat dissipated within the system is transferred away from the electronics using fluid flow pumped through the interface. It should be noted that when reference is made herein to fluid, this is not limited to liquid or any type of liquid, but can include, for example, air, gas, oil, etc. In general, the fluid is any type of substance that can flow through the integrated cooling channels to provide a cooling effect. The fluid may be selected based on the particular application. For example, an electronics cooling liquid may be used to cool electronics.

FIG. 1 shows an interface 20 constructed in accordance with various embodiments of the invention. The interface 20, for example, may be a connector that connects different components within a system. The interface 20 may include a housing 55 (e.g., a metal housing) having interface components therein as described in more detail below. For example, the interface 20 may be a connector end of an ultrasound probe that connects the electronics within the ultrasound probe to an ultrasound scanner or control unit of the ultrasound system. The interface 20 includes on one side 22 an electrical connection member 24 that connects to a complementary portion of a host machine, for example, a control system. The electrical connection member 24 may be configured based on the system to which the interface 20 is to be connected. For example, the size, shape, number of pins 26 (e.g., electrical conductors) may be varied as desired or needed. Additionally, the electrical connection member 24 may extend from the one side 22, for example, forming an engagement portion or may be recessed within the interface 20 to receive therein a connection member of the system to which the interface 20 is to be connected.

The interface 20 also includes a cooling system 21 therein (shown in FIG. 2) that includes on the side 22 a tubing loop 23 (e.g., an elastic tubing loop) that extends from the side 22 and circulates fluid through the interface 20 as described in more detail below. The tubing loop 23 is configured in various embodiments, and in particular, sized and shaped, to received in the loop a pump 70, for example, a peristaltic pump that operates to pump fluid through the tubing loop 23, and accordingly, into and out from the interface 20 when engaged with the tubing loop 23. However, it should be noted that different types of pumps may be used and the various embodiments are not limited to use with peristaltic or other positive displacement types of pumps.

The interface 20 on another side 28 includes tubing 30, for example, elastic tubing that connects the interface 20 to electronics 32 to be cooled. The tubing 30 includes therein means therein that provides both electrical connection, via electrical wires 34 to the electronics 32, and a fluid flow path through one or more fluid tubes 36 (e.g., rubber, silicone or plastic tubes), to the electronics 32 or to a region in proximity to the electronics 32. The tubing 30 may be any type of covering or enclosure surrounding the electrical wires 34 and fluid tubes 36. Separate tubing 30 may be provided for each of the electrical wires 34 and fluid tubes 36 or optionally no tubing 30 may be provided. The electrical wires 34 connect, for example, to electronic components 38 mounted on one or more electronic circuit boards 40 using any known connection means. In one embodiment, the one or more fluid tubes 36 also connect to the one or more electronic circuit boards 40 at ports 42 of the electronic circuit boards 40. The one or more electronic circuit boards 40 may include integrated fluid channels that circulate fluid therethrough. In this embodiment, the one or more electronic circuit boards 40 may be formed using a Low Temperature Co-fired Ceramics (LTCC) process. In particular, the one or more electronic circuit boards 40 may be formed as described in co-pending and commonly assigned U.S. patent application Ser. No. 12/032,940, entitled "Method and Apparatus for Cooling in Miniaturized Electronics," which is hereby incorporated by reference in its entirety.

It should be noted that the fluid tubes 36 optionally may be positioned adjacent or proximate the electronics 32 to provide fluid flow in close proximity to the electronic components 38. Fluid connectors 44 may also connect different ports 46 of different electronic circuit boards 40 to provide fluid flow between the different electronic circuit boards 40. However, the various embodiments are not limited to this type of serial fluid flow connection, but instead may have a parallel connection wherein each electronic circuit board 40 is connected to a different fluid tube 36. It also should be noted that there is not necessarily a one to one relation between the fluid tubes 36 from the interface 20 and the fluid tubes 36 at the electronics 32. For example, a single fluid tube 36 may be provided at the side 28 of the interface 20 and the fluid tube 36 split or divided into two different fluid tubes 36 at the electronics 32 for connection to different electronic circuit boards 40. However, there may be a one to one relation, wherein, for example, two fluid tubes 36 are provided at the side 28 of the interface 20 that extend to the electronics 32. The fluid tubes 36 may be formed of any suitable material (e.g., rubber or plastic) that allows fluid flow therethrough. For example, the fluid tubes 36 may be formed from materials based on whether the fluid flowing through the fluid tubes 36 is a liquid or gas, and further, the specific type of liquid or gas.

Figure 2:
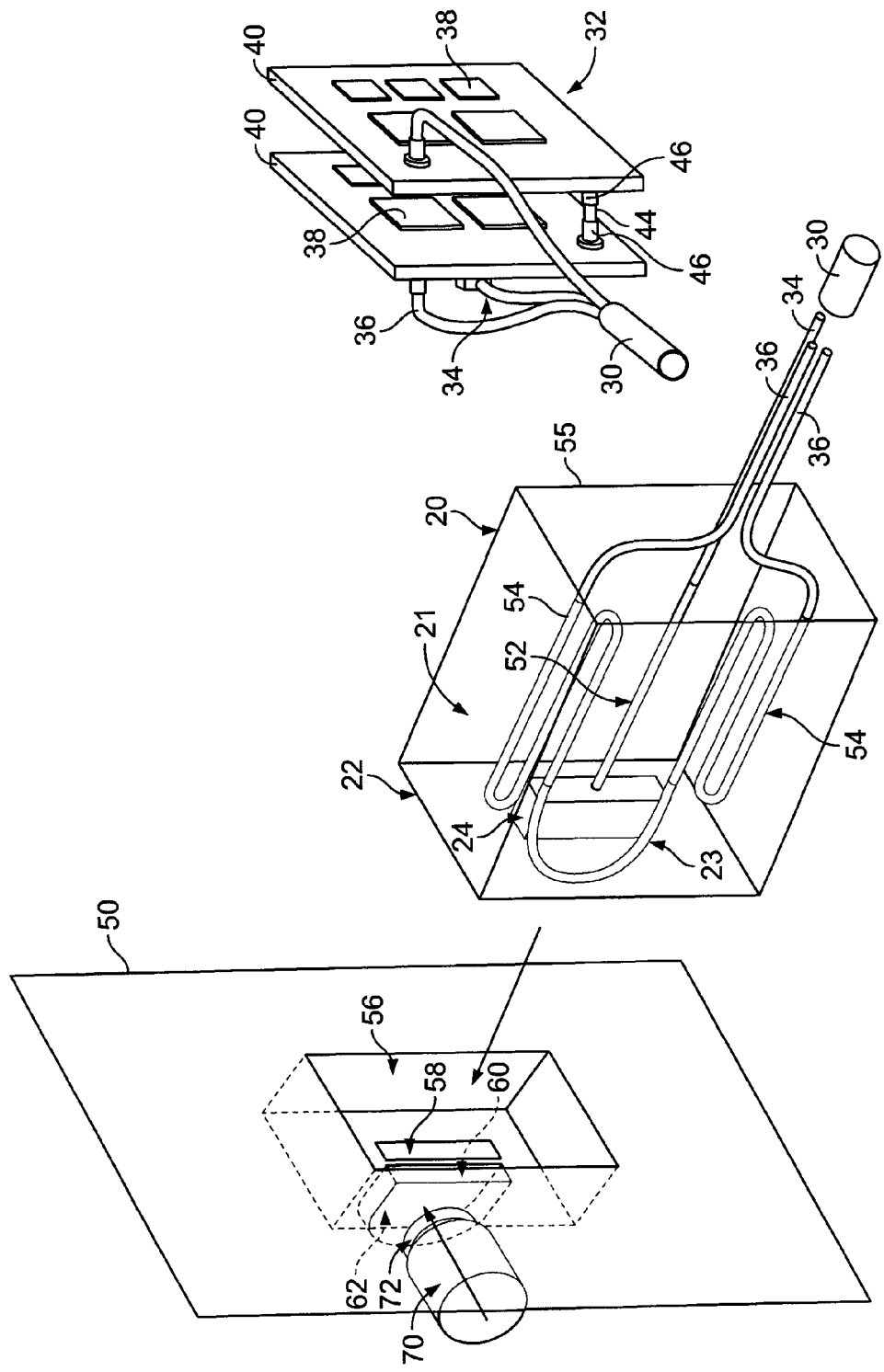
FIG. 2 is a diagram showing a host machine with a pump in connection with which the interface of FIG. 1 may be engaged.

FIG. 2 shows the interface 20 in combination with a host machine 50 to which the interface 20 connects. For example, the host machine 50 may be a ultrasound machine or scanner to which is connected a probe (not shown) that includes the interface 20 with the electronics 38 within the housing of the probe. The inside of the interface 20 is shown in FIG. 2. As can be seen, one or more electrical cables 52 within the interface 20 provides electrical connection and an electrical path between the electrical connection member 24 on the side 22 and the electrical wires 34 within the tubing 30. Also provided within the interface 20 is tubing, which in various embodiments is metal tubing 54 that provides a fluid path from the tubing loop 23 to the fluid tube 36. It should be noted that the metal tubing 54 may form different paths within the interface 20. For example, the metal tubing 54 may form a back and forth arrangement to circulate more fluid within the housing of the interface 20. The metal tubing 54 may be formed of any suitable metal (e.g., copper) or other thermally conducting material, which may be based on the type of fluid flowing therethrough. Also, the metal tubing 54 is thermally connected to a housing 55 of the interface 20. For example, the metal tubing 54 may be surrounded by a thermally conducting material that also contacts an inner surface of the housing 55. However, it should be noted that any suitable thermal conduction arrangement may be used, for example, such as heat conductors or heat pipes as are known.

The interface 20 is configured to connect to the host machine 50, for example, within a connection port 56 (e.g., a recessed portion) of the host machine 50. The connection port 56 may be provided in any type of configuration that allows secure connection of the interface 20 to the host machine 50. The connection port 56 generally includes an electrical connection member 58 that connects with the electrical connection member 24 of the interface 20 when the interface 20 is engaged to connection port 56. This complementary connection arrangement provides electrical connection from the host machine 50 to the electronics 32 through the interface 20. For example, in an ultrasound system as described in more detail below, the electrical connection provides an electrical signal path from the ultrasound system to the ultrasound probe to operate transducer elements in the probe scan head that are controlled using electronic components, for example, the electronics 32. The connection port 56 also includes a cavity 60 that receives therein the tube loop 23 when the interface is engaged to connection port 56.

The cavity 60 includes an open portion 62 for receiving therein a pump head 72 of the pump 70. Accordingly, after the interface 20 is engaged with the connection port 56, the pump 70 is inserted within the open portion 62 to engage the pump loop 23, which in this embodiment is a peristaltic or positive displacement pump arrangement wherein the pump loop 23 surround the pump head 72. In one embodiment, the pump 70 is manually inserted within the open portion 62, for example, by a user pushing the pump 70 therein or operating a manual lever or arm to move the pump 70 into the open portion 62. In another embodiment, the pump 70 is automatically inserted within the open portion 62, for example, using an electric motor configured to move the pump head 72 into position such that the pump head 72 engages the tube loop 23.

Figure 3:
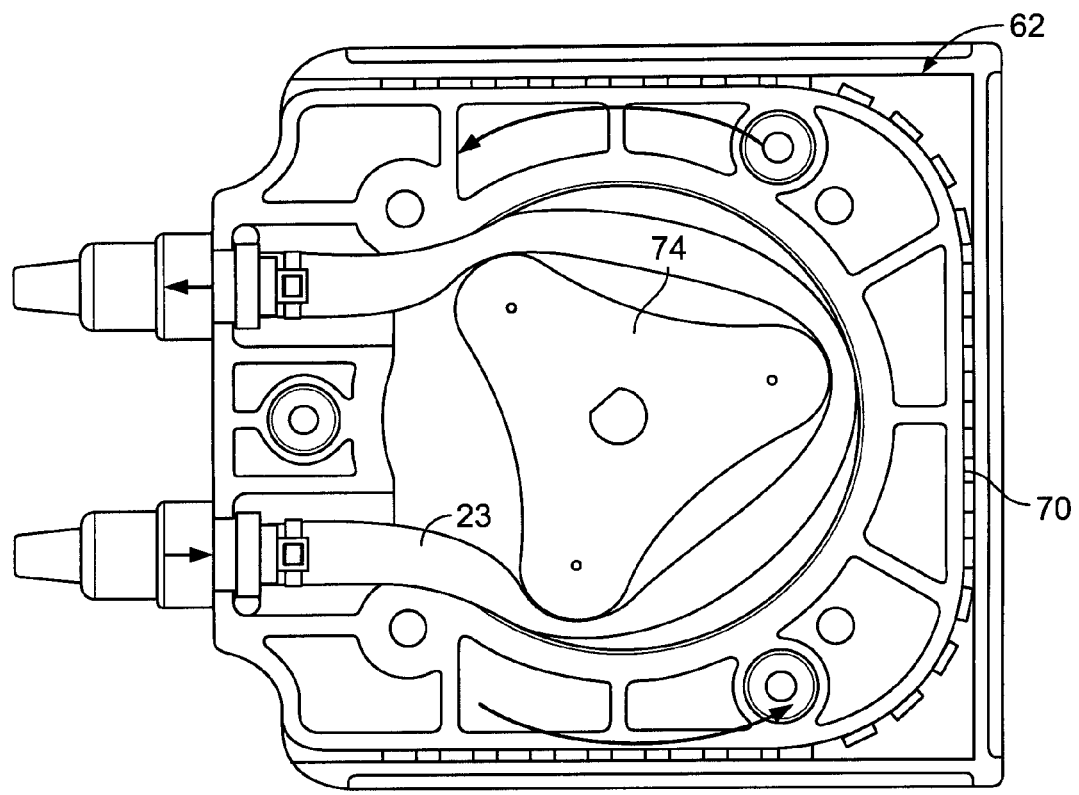
FIG. 3 is a plan view of the pump of FIG. 2 constructed in accordance with various embodiments of the invention.

The pump 70 may be any type of pump that circulates fluid through the loop tube 23, metal tubing 54 and the fluid tubes 36. For example, as shown in FIG. 3, the pump 70 may be a peristaltic pump having a rotor 74 that may include rollers or similar members attached thereto to compress the tube loop 23. As the rotor 74 turns, fluid within the loop tube 23 is circulated. The pump 70 may be located within the host machine 50 with the pump 70 moved into engagement with the tube loop 23 all within the host machine 50. For example, in an ultrasound system, as the pump head 72, which may include the rotor 74, presses against the tubing loop 23, the rotor 74 starts to rotate as illustrated by the arrows. Rotation together with the squeezing force against the tubing forces fluid to flow in to one direction inside the tubing, which forms a closed loop between, for example, the transducer end having the electronics 32 therein and the interface 20, which forms the connector end of the probe. Circulation of fluid is thereby provided in a closed circulation path. The fluid flowing inside the tubing transfers heat away from the transducer to the interface 20 where the heat is conducted as described herein. As the fluid transfers the heat to the host machine 50, the fluid cools down and is returned back to the transducer end of the probe.

Thus, in operation, the interface 20 provides electrical connection to the electronics 38 and also allows fluid flow to transfer heat generated by the electronics 38. In particular, using the various embodiments of the invention, when the tube loop 23 engages the pump 70, which causes fluid flow, the metal tubing 54 that is thermally connected to the housing 55 of the interface 20 transfers heat from the liquid within the metal tubing 54 to surfaces of the housing 55. This transferred heat is then dissipated into the surrounding air. Also, when the interface 20 is engaged to the connection port 56 of the host machine 50, the interface 20 essentially provides a thermal connection to the thermally conducting surfaces of the host machine 50, for example, the metal surfaces of the host machine 50 (e.g., metal surfaces of an ultrasound scanner). The heat is then dissipated into the surrounding air. Thus, heat is transferred from the electronics 32, which may be located, for example, in the transducer end of a scan head of an ultrasound probe, within the circulating fluid, through the interface 20 (that dissipates the transferred heat) into the housing of the host machine 50, where the heat also may be dissipated into the surrounding air.

It should be noted that although the various embodiments are described below in connection with an ultrasound system, the various embodiments are not limited to ultrasound systems or diagnostic imaging systems. The various embodiments may be implemented as part of or in any system where cooling of electronics is desired or needed. For example, the various embodiments may be used to cool any type of processor, electronic processing device, processing machine, etc. such as the processors or integrated circuits associated with a personal computer (PC) system.

At least one technical effect of the various embodiments is transferring heat generated from electronics using fluid flow from the electronics through an interface and into a host machine. Heat transferred from the electronics is dissipated into the surrounding air from the interface and the host machine. Accordingly, no cooling ribs or separate aluminum body for the pump are needed. Thus, and for example, a hand held ultrasonic transducer can be made smaller, lighter and containing considerably less handwork. For example, in an ultrasound system, the connector end of the probe (e.g., the interface) becomes much smaller, lighter and less expensive because the pump does not have to be included therein. Power consumption and heat balance also may be improved as the pump is moved into the host machine. Reliability also increases as the tubing forms a closed loop with less connections and connection joints and as the pump is no longer part of the probe.

Figure 4:
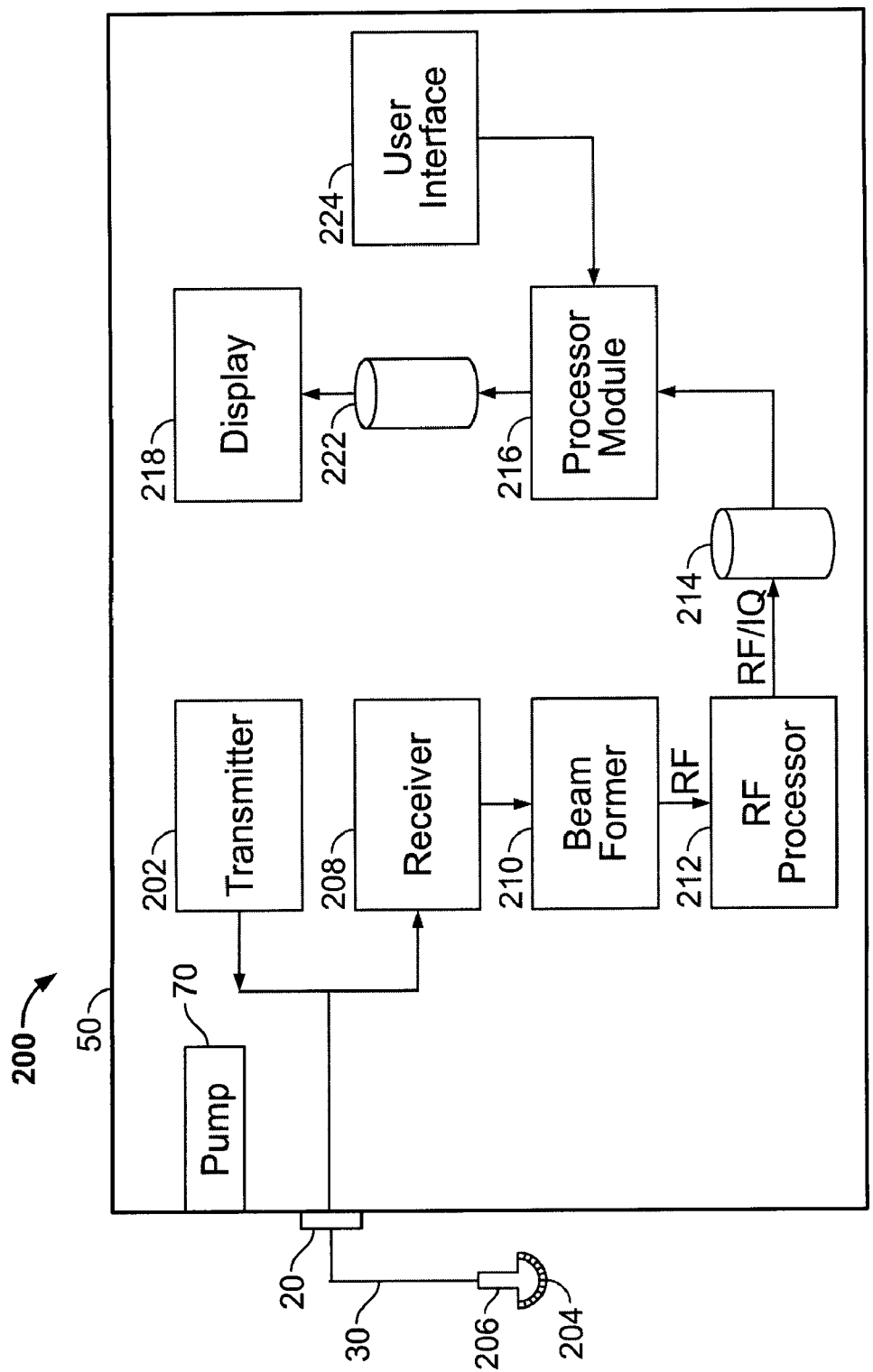
FIG. 4 is a block diagram of an ultrasound system having electronics from which heat may be transferred in accordance with various embodiments of the invention.

In particular, the various embodiments may be used to transfer heat from the electronics associated with a probe having a transducer 206 (or transducer array) in an ultrasound system 200 as shown in FIG. 4. The ultrasound system 200 includes an ultrasound scanner, which is the host machine 50. The ultrasound system 200 includes a transmitter 202 that drives an array of elements 204 (e.g., piezoelectric elements) within a transducer 206 to emit pulsed ultrasonic signals into a body. The elements 204 may be arranged, for example, in one or two dimensions and may form part of a probe that includes the interface 20 that connects to the host machine 50. A variety of geometries may be used. When connected to the host machine 50, the pump 70 of the host machine 50 is also engaged by the interface 20 as described herein. The ultrasonic signals are back-scattered from structures in the body, like fatty tissue or muscular tissue, to produce echoes that return to the elements 204. The echoes are received by a receiver 208. The received echoes are passed through a beamformer 210 that performs beamforming and outputs an RF signal. The RF signal then passes through an RF processor 212. Alternatively, the RF processor 212 may include a complex demodulator (not shown) that demodulates the RF signal to form IQ data pairs representative of the echo signals. The RF or IQ signal data may then be routed directly to a memory 214 for storage.

The ultrasound system 200 also includes a processor module 216 to process the acquired ultrasound information (e.g., RF signal data or IQ data pairs) and prepare frames of ultrasound information for display on display 218. The processor module 216 is adapted to perform one or more processing operations according to a plurality of selectable ultrasound modalities on the acquired ultrasound information. Acquired ultrasound information may be processed and displayed in real-time during a scanning session as the echo signals are received. Additionally or alternatively, the ultrasound information may be stored temporarily in memory 214 or memory 222 during a scanning session and then processed and displayed in an off-line operation.

A user interface 224 may be used to input data into the system 200 and to adjust settings and control operation of the processor module 216. One or both of memory 214 and memory 222 may store two-dimensional (2D) and/or three-dimensional (3D) datasets of the ultrasound data, where such datasets are accessed to present 2D and/or 3D images. Multiple consecutive 3D datasets may also be acquired and stored over time, such as to provide real-time 3D or four-dimensional (4D) display. The images may be modified and the display settings of the display 218 also manually adjusted using the user interface 224.

Figure 5:
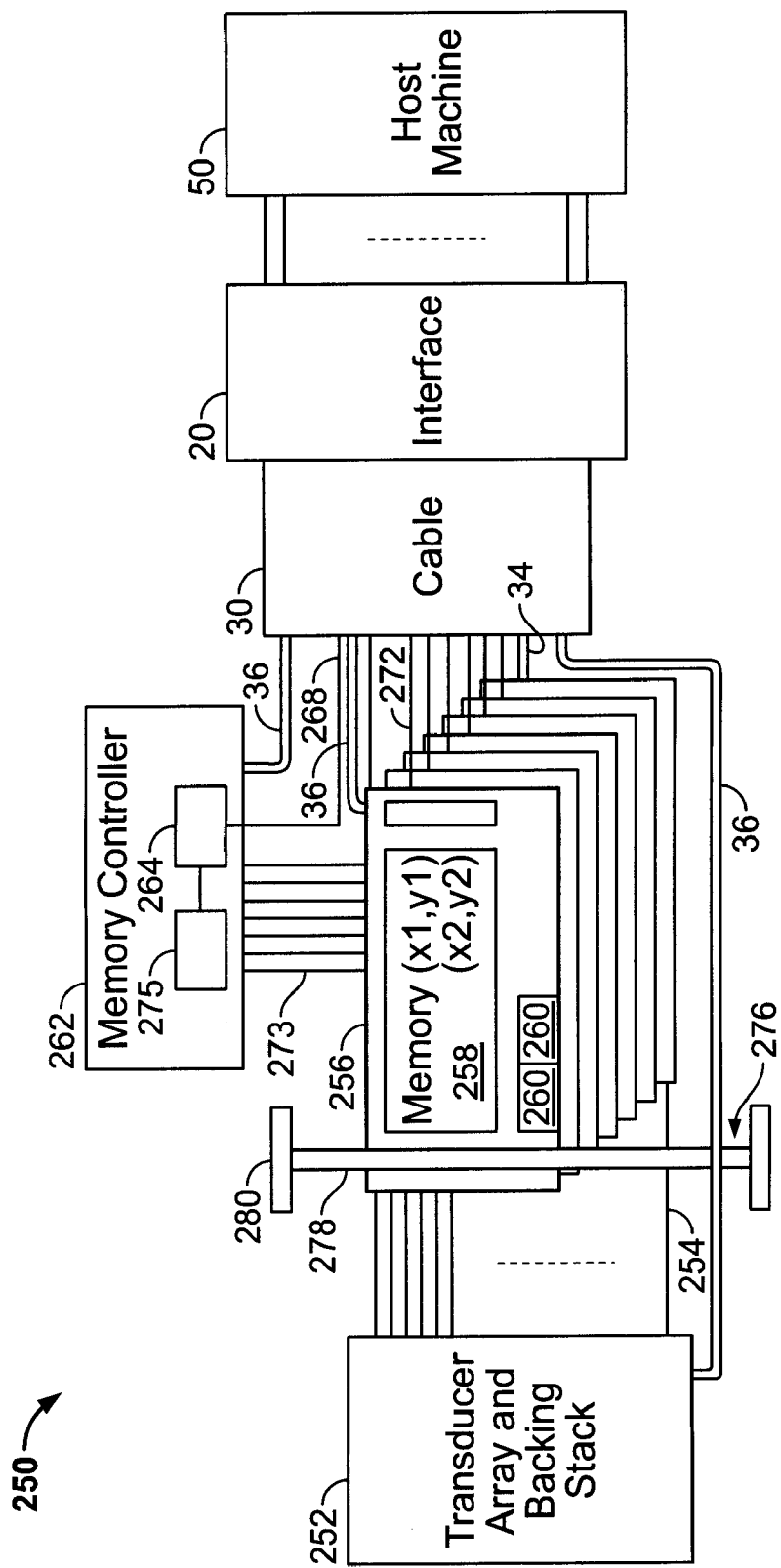
FIG. 5 is a block diagram of an ultrasound probe in communication with a host system for use with the ultrasound system shown in FIG. 4 and having electronics from which heat may be transferred in accordance with various embodiments of the invention.

In particular, the various embodiments of the invention may be implemented to transfer heat from the electronics of an ultrasound probe 250 shown in FIG. 5 that may be used in connection with the ultrasound systems 200. The ultrasound probe 250 includes a transducer array and backing stack 252 (the "transducer array 252"), transducer flex cables 254, which may be formed as a scan head cable, and multiple processing boards 256 that support processing electronics and formed with integrated channels (shown in FIGS. 1 and 2). Each processing board 256 may includes a location memory 258 (which may include geometry RAM, encoder RAM, location registers and control registers as noted below) and signal processors 260. A location memory controller 262 (e.g., a general purpose CPU, microcontroller, PLD, or the like) also may be provided and includes a communication interface 264.

The communication interface 264 establishes data exchange with a host system 266 over communication lines 268 (e.g., digital signal lines) and through a system cable that may form part of the tubing 30. Additionally, in an exemplary embodiment, the system cable includes coaxial cables 272, that may form all or part of the electrical wires 34, that connect to the processing boards 256 to communicate transmit pulse waveforms to the transducer array 252 and communicate receive signals, after beamforming, to the host system 266. The probe 250 also may include the interface 20, through which the probe 250 connects to the host machine 50. This connection arrangement, as described in more detail above, also provides cooling of the electronics using fluid tubes 36 that convey fluid therethrough.

A clamp 276 may be provided to hold the transducer flex cables 254 against the processing boards 256. The clamp 276 thereby aids in establishing electrical connectivity between the transducer flex cables 254 and the processing boards 256. The clamp 276 may include a dowel pin 278 and a bolt 280, although other implementations are also suitable.

For every ultrasound beam, the location memory controller 262 connects via digital signal lines 273 (e.g., carried by a separate flex cable) to each location memory 258 on each processing board 256. The location memory controller 262 communicates the spatial location information into each location memory 258 for each receive aperture processed by the signal processors 260 on the processing boards 256. The digital signal lines 273 may include, for example, a clock line for each processing board 256, a serial command data line for each processing board 256, two data lines (for a total of fourteen data lines) connected to each processing board 256, an output enable for one or more of the signal processors 260, and a test signal.

The location memory controller 262 communicates with the host system 266 over the digital signal lines 273 that may form part of, for example, a synchronous serial port. To that end, the communication interface 264 and digital signal lines 273 may implement a low voltage differential signal interface, for example, including a coaxial cable with a grounded shield and center signal wire. The location memory controller 262 includes a block of cache memory 275, for example, 1-8 MBytes of static random access memory (SRAM).

However, and as noted above, the various embodiments are not limited to use in connection with an ultrasound system or any medical imaging system. The various embodiments may be implemented in connection with any system that includes electronic components, such as electronic circuit boards.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An interface for cooling electronics, the interface comprising:
    a housing having tubing (i) therein to transfer heat from liquid flowing in the tubing and (ii) extending therefrom and having an outer surface configured to engage a pump, the tubing forming a closed circulation path; and
    an electrical connection member configured to provide electrical connection through the housing and to the electronics.

2. An interface in accordance with claim 1 wherein the tubing inside the housing comprises metal tubing.

3. An interface in accordance with claim 1 wherein the tubing inside the housing comprises thermally conducting material.

4. An interface in accordance with claim 1 wherein the tubing inside the housing is thermally connected to the housing.

5. An interface in accordance with claim 1 wherein the tubing extending from the housing and the electrical connection member are positioned on one side of the housing and configured to engage a host machine having the pump therein.

6. An interface in accordance with claim 5 wherein the host machine comprises an ultrasound scanner.

7. An interface in accordance with claim 5 wherein tubing and electrical wires extend from another side of the connector, the electrical wires connected to the electrical connection member on the one side and the tubing and electrical wires configured to connect to the electronics.

8. An interface in accordance with claim 7 wherein the electronics comprise electronics within an ultrasound probe and the housing comprises a connector for the ultrasound probe.

9. An interface in accordance with claim 1 wherein the housing is configured to engage a connection port of a host machine.

10. An interface in accordance with claim 1 wherein the tubing extending from the housing comprises elastic tubing.

11. An interface in accordance with claim 1 wherein the tubing is configured to be compressed by the pump to provide fluid flow inside the tubing.

12. An interface in accordance with claim 1 wherein the tubing is compressible and configured to provide fluid flow therein when a squeezing force is applied by the pump.

13. An interface for cooling electronics, the interface comprising:
    a housing having tubing (i) therein to transfer heat from liquid flowing in the tubing and (ii) extending therefrom and configured to engage a pump, the tubing forming a closed circulation path, wherein the tubing extending from the housing comprises a loop for engaging therein the pump; and
    an electrical connection member configured to provide electrical connection through the housing and to the electronics.

14. An ultrasound system comprising:
    an ultrasound scanner having a pump and including a connection port having an open portion therein; and
    a probe having a connector including a cooling system therein, the connector configured to engage the connection port and wherein engagement of the connector with the connection port provides (i) electrical connection between the ultrasound scanner and the probe and (ii) connection of the cooling system to the pump of the ultrasound scanner with tubing extending into the open portion of the connection port to engage the pump.

15. An ultrasound system in accordance with claim 14 wherein the cooling system comprises tubing within the connector and tubing extending from an end of the connector to engage the pump when the connector engages the connection port.

16. An ultrasound system in accordance with claim 15 wherein the pump manually engages the tubing extending from the end of the connector.

17. An ultrasound system in accordance with claim 15 wherein the pump automatically engages the tubing extending from the end of the connector.

18. An ultrasound system in accordance with claim 15 wherein the tubing inside the connector comprises a thermally conducting material thermally connected to a housing of the connector.

19. An ultrasound system in accordance with claim 14 wherein the cooling system is thermally connected to thermally conducting surfaces of the ultrasound scanner when the connector engages the connection port.

20. An ultrasound system in accordance with claim 14 wherein the connection port comprises an electrical connection member configured to connect to the connector of the probe.

21. An ultrasound system comprising:
    an ultrasound scanner having a pump and including a connection port; and
    a probe having a connector including a cooling system therein, the connector configured to engage the connection port and wherein engagement of the connector with the connection port provides (i) electrical connection between the ultrasound scanner and the probe and (ii) connection of the cooling system to the pump of the ultrasound scanner, wherein the cooling system comprises tubing within the connector and tubing extending from an end of the connector to engage the pump when the connector engages the connection port, and wherein the tubing extending from the end of the connector comprises a tubing loop.

22. A method of cooling an ultrasound system, the method comprising:
    circulating fluid within a closed tubing path that extends from a connector of an ultrasound probe of the ultrasound system to electronics within the ultrasound probe, the fluid circulated using a pump located within an ultrasound scanner of the ultrasound system; and
    thermally connecting tubing within the connector with a housing of the connector by surrounding the tubing with a thermally conducting material and wherein the connector is thermally connected to the ultrasound scanner when the connector of the ultrasound probe engages the ultrasound scanner.

* * * * *